United States Patent
OuYang et al.

(10) Patent No.: US 10,045,686 B2
(45) Date of Patent: Aug. 14, 2018

(54) TISSUE VISUALIZATION AND MODIFICATION DEVICE

(71) Applicant: Trice Medical, Inc., Wilmington, DE (US)

(72) Inventors: Xiaolong OuYang, Palo Alto, CA (US); James S. Cybulski, Palo Alto, CA (US); Fred R. Seddiqui, Los Altos, CA (US)

(73) Assignee: Trice Medical, Inc., Wilmington, DE (US)

( * ) Notice: Subject to any disclaimer, the term of this patent is extended or adjusted under 35 U.S.C. 154(b) by 378 days.

(21) Appl. No.: 13/739,664

(22) Filed: Jan. 11, 2013

(65) Prior Publication Data

US 2013/0296648 A1    Nov. 7, 2013

Related U.S. Application Data

(63) Continuation of application No. 12/269,770, filed on Nov. 12, 2008.

(51) Int. Cl.
*A61B 1/018* (2006.01)
*A61B 1/015* (2006.01)
(Continued)

(52) U.S. Cl.
CPC .......... *A61B 1/042* (2013.01); *A61B 1/00087* (2013.01); *A61B 1/00154* (2013.01);
(Continued)

(58) Field of Classification Search
CPC ............ A61B 1/00181; A61B 1/00087; A61B 1/00193; A61B 1/00154; A61B 1/0125;
(Continued)

(56) References Cited

U.S. PATENT DOCUMENTS 3,835,842 A * 9/1974 Iglesias .............. A61B 1/00091
                                                600/105
3,871,358 A * 3/1975 Fukuda .............. A61B 1/00154
                                                600/585
(Continued)

FOREIGN PATENT DOCUMENTS

AU     2015204444      1/2018
CN      2557085 Y      6/2003
(Continued)

OTHER PUBLICATIONS

U.S. Appl. No. 14/308,167, filed Jun. 18, 2014, Kienzle et al.
(Continued)

*Primary Examiner* — John P Leubecker
(74) *Attorney, Agent, or Firm* — Knobbe, Martens, Olson & Bear LLP

(57) ABSTRACT

A tissue visualization and modification device may include a rigid access body having a longitudinal axis, an internal passageway extending from the proximal end to the distal end, and an access body imaging sensor positioned on the distal end of the body and protruding inward beyond an inner wall into the internal passageway. An elongated member may be slidably positioned within the rigid access body. The elongated member may include, when viewed substantially along the longitudinal axis, a dissection electrode in the shape of a semicircle, an irrigation channel positioned within the semicircle, an aspiration channel positioned partially within the semicircle and adjacent the irrigation channel, first and second illumination elements positioned adjacent the respective tips of the semicircle and an elongated member imaging sensor positioned adjacent the aspiration channel.

10 Claims, 6 Drawing Sheets

(51) Int. Cl.
*A61B 1/04* (2006.01)
*A61B 1/06* (2006.01)
*A61B 1/012* (2006.01)
*A61B 5/00* (2006.01)
*A61B 18/00* (2006.01)
*A61B 1/00* (2006.01)
*A61B 17/00* (2006.01)

(52) U.S. Cl.
CPC ........ *A61B 1/00181* (2013.01); *A61B 1/0125* (2013.01); *A61B 5/0084* (2013.01); *A61B 1/00094* (2013.01); *A61B 1/00193* (2013.01); *A61B 1/015* (2013.01); *A61B 2017/00296* (2013.01); *A61B 2018/00982* (2013.01)

(58) Field of Classification Search
CPC ... A61B 1/00135; A61B 1/0684; A61B 1/317; A61B 1/00094; A61B 1/015; A61B 2017/00296; A61B 2017/0034; A61B 2018/00982; A61B 2018/1405; A61B 2018/142
See application file for complete search history.

(56) References Cited

U.S. PATENT DOCUMENTS

| | | | |
|---|---|---|---|
| 4,069,823 A | 1/1978 | Isakov et al. | |
| 4,519,391 A | 5/1985 | Murakoshi | |
| 4,624,243 A | 11/1986 | Lowery et al. | |
| 4,646,738 A | 3/1987 | Trott | |
| 4,651,201 A | 3/1987 | Schoolman | |
| 4,678,459 A | 7/1987 | Onik et al. | |
| 4,697,210 A | 9/1987 | Toyota et al. | |
| 4,700,702 A | 10/1987 | Nilsson | |
| 4,750,902 A | 6/1988 | Wuchinich et al. | |
| 4,845,555 A | 7/1989 | Yabe et al. | |
| 4,919,112 A | 4/1990 | Siegmund | |
| 5,088,676 A | 2/1992 | Orchard et al. | |
| 5,131,382 A | 7/1992 | Meyer | |
| 5,170,775 A | 12/1992 | Tagami | |
| 5,178,130 A * | 1/1993 | Kaiya | 600/109 |
| 5,188,093 A | 2/1993 | Lafferty et al. | |
| 5,190,028 A | 3/1993 | Lafferty et al. | |
| 5,195,541 A | 3/1993 | Obenchain | |
| 5,228,430 A | 7/1993 | Sakamoto | |
| 5,242,441 A | 9/1993 | Avitall | |
| 5,269,785 A | 12/1993 | Bonutti | |
| 5,291,010 A * | 3/1994 | Tsuji | A61B 1/05 250/208.1 |
| 5,312,407 A | 5/1994 | Carter | |
| 5,313,962 A | 5/1994 | Obenchain | |
| 5,318,589 A | 6/1994 | Lichtman | |
| 5,373,312 A | 6/1994 | Bala | |
| 5,334,183 A | 8/1994 | Wuchinich | |
| 5,351,678 A | 10/1994 | Clayton et al. | |
| 5,354,302 A | 10/1994 | Ko | |
| 5,365,267 A * | 11/1994 | Edwards | H04N 9/735 348/223.1 |
| 5,368,015 A | 11/1994 | Wilk | |
| 5,369,525 A | 11/1994 | Bala et al. | |
| 5,373,317 A | 12/1994 | Salavi et al. | |
| 5,373,392 A | 12/1994 | Bala | |
| 5,383,888 A | 1/1995 | Zvenyatsky et al. | |
| 5,395,312 A | 3/1995 | Desai | |
| 5,395,313 A | 3/1995 | Naves et al. | |
| 5,403,276 A | 4/1995 | Schechter et al. | |
| 5,403,342 A | 4/1995 | Tovey et al. | |
| 5,406,940 A | 4/1995 | Melzer et al. | |
| 5,417,203 A | 5/1995 | Tovey et al. | |
| 5,423,312 A | 6/1995 | Siegmund et al. | |
| 5,425,355 A | 6/1995 | Kulick | |
| 5,476,473 A | 12/1995 | Heckele | |
| 5,484,433 A | 1/1996 | Taylor et al. | |
| 5,494,483 A | 2/1996 | Adair | |
| 5,500,012 A | 3/1996 | Brucker et al. | |
| 5,512,036 A | 4/1996 | Tamburrino et al. | |
| 5,518,502 A | 5/1996 | Kaplan et al. | |
| 5,547,455 A | 8/1996 | McKenna et al. | |
| 5,569,158 A | 10/1996 | Suzuki et al. | |
| 5,577,992 A * | 11/1996 | Chiba | A61B 1/0056 600/116 |
| 5,582,575 A | 12/1996 | Heckele et al. | |
| 5,591,192 A | 1/1997 | Pivitera et al. | |
| 5,601,525 A | 2/1997 | Okada | |
| 5,630,784 A | 5/1997 | Siegmund et al. | |
| 5,630,837 A | 5/1997 | Crowley | |
| 5,643,294 A | 7/1997 | Tovey et al. | |
| 5,647,840 A | 7/1997 | D'Amelio et al. | |
| 5,674,191 A | 10/1997 | Edwards et al. | |
| 5,695,513 A | 12/1997 | Johnson et al. | |
| 5,704,534 A | 1/1998 | Huitema et al. | |
| 5,707,382 A | 1/1998 | Sierocuk et al. | |
| 5,766,194 A | 1/1998 | Smith | |
| 5,713,505 A | 2/1998 | Huitema | |
| 5,722,403 A | 3/1998 | McGee et al. | |
| 5,735,792 A | 4/1998 | Vanden Hoeck et al. | |
| 5,757,458 A | 5/1998 | Miller et al. | |
| 5,766,199 A | 6/1998 | Heisler et al. | |
| 5,766,200 A | 6/1998 | Mazurek et al. | |
| 5,785,647 A | 7/1998 | Tompkins et al. | |
| 5,788,636 A | 8/1998 | Curley | |
| 5,807,240 A * | 9/1998 | Muller | A61B 1/00094 600/105 |
| 5,818,527 A * | 10/1998 | Yamaguchi et al. | 348/335 |
| 5,836,943 A | 11/1998 | Miller, III | |
| 5,857,961 A | 1/1999 | Vanden Hoeck et al. | |
| 5,864,359 A * | 1/1999 | Kazakevich | 348/45 |
| 5,868,664 A | 2/1999 | Speier et al. | |
| 5,873,814 A | 2/1999 | Adair | |
| 5,873,816 A | 2/1999 | Ishii | |
| 5,873,817 A | 2/1999 | Adair | |
| 5,879,285 A | 3/1999 | Ishii | |
| 5,888,193 A | 3/1999 | Breidental et al. | |
| 5,902,272 A | 5/1999 | Eggers et al. | |
| 5,916,146 A | 6/1999 | Alotta et al. | |
| 5,928,137 A | 7/1999 | Crawford | |
| 5,929,901 A | 7/1999 | Adair et al. | |
| 5,941,817 A | 8/1999 | Crawford | |
| 5,976,075 A | 11/1999 | Beane et al. | |
| 5,976,076 A | 11/1999 | Kolff et al. | |
| 5,976,077 A | 11/1999 | Wittens et al. | |
| 5,986,693 A | 11/1999 | Adair et al. | |
| 6,001,084 A | 12/1999 | Riek et al. | |
| 6,043,839 A | 3/2000 | Adair et al. | |
| 6,045,549 A | 4/2000 | Smethers et al. | |
| 6,068,603 A | 5/2000 | Suzuki | |
| 6,080,101 A | 6/2000 | Tatsuno et al. | |
| 6,086,528 A | 7/2000 | Adair | |
| 6,053,923 A | 8/2000 | Veca et al. | |
| 6,099,465 A | 8/2000 | Inoue | |
| 6,112,123 A | 8/2000 | Kelleher et al. | |
| 6,110,127 A | 9/2000 | Suzuki | |
| 6,113,614 A | 9/2000 | Mears | |
| 6,126,592 A | 10/2000 | Proch et al. | |
| 6,129,662 A | 10/2000 | Li et al. | |
| 6,142,957 A | 11/2000 | Diamond et al. | |
| 6,149,646 A | 11/2000 | West, Jr. et al. | |
| 6,156,033 A | 12/2000 | Tu et al. | |
| 6,211,904 B1 | 4/2001 | Adair et al. | |
| 6,234,955 B1 | 5/2001 | Silverman et al. | |
| 6,241,727 B1 | 6/2001 | Tu et al. | |
| 6,251,120 B1 | 6/2001 | Dorn | |
| 6,261,226 B1 | 7/2001 | McKenna et al. | |
| 6,264,670 B1 | 7/2001 | Chin | |
| 6,275,255 B1 | 8/2001 | Adair et al. | |
| 6,277,137 B1 | 8/2001 | Chin | |
| 6,310,642 B1 | 10/2001 | Adair et al. | |
| 6,315,712 B1 | 11/2001 | Rovegno | |
| 6,316,215 B1 | 11/2001 | Adair et al. | |
| 6,322,494 B1 | 11/2001 | Bullicant et al. | |
| 6,331,165 B1 | 12/2001 | Turturro et al. | |
| 6,332,881 B1 | 12/2001 | Carner et al. | |
| 6,371,909 B1 | 4/2002 | Hoeg et al. | |

(56) References Cited

U.S. PATENT DOCUMENTS

| | | | |
|---|---|---|---|
| 6,387,043 B1 * | 5/2002 | Yoon | 600/109 |
| 6,390,972 B1 | 5/2002 | Speier et al. | |
| 6,419,626 B1 | 7/2002 | Yoon | |
| 6,419,627 B1 | 7/2002 | Ben Nun | |
| 6,419,654 B1 | 7/2002 | Kadan | |
| 6,424,369 B1 | 7/2002 | Adair et al. | |
| 6,447,445 B1 * | 9/2002 | Hirano | A61B 1/0008 600/129 |
| 6,452,626 B1 | 9/2002 | Adair et al. | |
| 6,458,140 B2 | 10/2002 | Akin et al. | |
| 6,459,481 B1 * | 10/2002 | Schaack | A61B 5/1076 356/241.1 |
| 6,464,633 B1 | 10/2002 | Hosoda et al. | |
| 6,464,711 B1 | 10/2002 | Emans et al. | |
| 6,468,274 B1 | 10/2002 | Alleynne et al. | |
| 6,478,730 B1 | 11/2002 | Bala et al. | |
| 6,491,690 B1 | 12/2002 | Goble et al. | |
| 6,527,753 B2 * | 3/2003 | Sekine et al. | 604/264 |
| 6,533,749 B1 | 3/2003 | Mitusina et al. | |
| 6,544,194 B1 | 4/2003 | Kortenbach et al. | |
| 6,561,973 B1 | 5/2003 | Bala | |
| 6,569,085 B2 | 5/2003 | Kortenbach et al. | |
| 6,572,578 B1 | 6/2003 | Blanchard | |
| 6,583,240 B2 | 6/2003 | Wang et al. | |
| 6,585,734 B2 | 7/2003 | Levinson | |
| 6,602,247 B2 | 8/2003 | Lalonde | |
| 6,602,248 B1 | 8/2003 | Sharps et al. | |
| 6,605,087 B2 | 8/2003 | Swartz et al. | |
| 6,607,529 B1 | 8/2003 | Jones et al. | |
| 6,623,437 B2 | 9/2003 | Hinchliffe et al. | |
| 6,632,227 B2 | 10/2003 | Adams | |
| 6,652,522 B1 | 11/2003 | Cucin | |
| 6,656,132 B1 | 12/2003 | Ouchi | |
| 6,656,195 B2 | 12/2003 | Peters et al. | |
| 6,660,011 B2 | 12/2003 | Levinson | |
| 6,675,033 B1 | 1/2004 | Lardo et al. | |
| 6,679,838 B1 | 1/2004 | Bala | |
| 6,682,535 B2 | 1/2004 | Hoogland | |
| 6,689,130 B2 | 2/2004 | Arai et al. | |
| 6,692,432 B1 | 2/2004 | Yarush et al. | |
| 6,695,772 B1 | 2/2004 | Bon et al. | |
| 6,726,684 B1 | 4/2004 | Woloszko et al. | |
| 6,750,037 B2 | 6/2004 | Adair et al. | |
| 6,764,439 B2 | 7/2004 | Schaaf et al. | |
| 6,805,715 B2 | 10/2004 | Reuter et al. | |
| 6,820,791 B2 | 11/2004 | Adams | |
| 6,832,984 B2 | 12/2004 | Stelzer et al. | |
| 6,833,000 B2 | 12/2004 | Levinson | |
| 6,835,198 B2 | 12/2004 | Bonutti | |
| 6,837,887 B2 | 1/2005 | Woloszko et al. | |
| 6,862,036 B2 | 3/2005 | Adair et al. | |
| 6,863,651 B2 | 3/2005 | Remijan et al. | |
| 6,885,801 B1 | 4/2005 | Shankar et al. | |
| 6,893,436 B2 | 5/2005 | Woodard et al. | |
| 6,899,672 B2 | 5/2005 | Chin et al. | |
| 6,902,526 B2 | 6/2005 | Katzman | |
| 6,982,740 B2 | 1/2006 | Adair et al. | |
| 6,982,742 B2 | 1/2006 | Adair et al. | |
| 6,997,941 B2 | 2/2006 | Sharkey et al. | |
| 7,002,621 B2 | 2/2006 | Adair et al. | |
| 7,004,938 B2 | 2/2006 | Ormsby et al. | |
| 7,030,904 B2 | 4/2006 | Adair et al. | |
| 7,060,028 B2 | 6/2006 | Luloh et al. | |
| 7,094,200 B2 | 8/2006 | Katzman | |
| 7,108,657 B2 | 9/2006 | Irion et al. | |
| 7,137,981 B2 | 11/2006 | Long | |
| 7,156,559 B2 | 1/2007 | Gauthier, Jr. et al. | |
| 7,160,247 B2 | 1/2007 | Deppmeier et al. | |
| 7,160,295 B1 | 1/2007 | Garito et al. | |
| 7,169,147 B2 | 1/2007 | Nosel | |
| 7,179,255 B2 | 2/2007 | Lettice et al. | |
| 7,198,635 B2 | 4/2007 | Danek et al. | |
| 7,214,183 B2 | 5/2007 | Miyake | |
| 7,258,663 B2 | 8/2007 | Doguchi et al. | |
| 7,269,344 B2 | 9/2007 | Nishioka et al. | |
| 7,270,658 B2 | 9/2007 | Wolozsko et al. | |
| 7,318,823 B2 | 1/2008 | Sharps et al. | |
| 7,320,688 B2 | 1/2008 | Foley et al. | |
| RE40,156 E | 3/2008 | Sharps et al. | |
| 7,435,010 B2 | 10/2008 | Gauthier, Jr. et al. | |
| 7,453,984 B2 | 11/2008 | Chen et al. | |
| 7,491,168 B2 | 2/2009 | Raymond et al. | |
| 7,572,578 B2 | 2/2009 | Blanchard | |
| 7,689,268 B2 | 3/2010 | Marshik-Geurts et al. | |
| 7,699,773 B2 | 4/2010 | Forkey et al. | |
| 7,708,689 B2 | 5/2010 | Deppmeier et al. | |
| 7,857,755 B2 | 12/2010 | Kupferschmid et al. | |
| 7,918,787 B2 | 4/2011 | Saadat | |
| 7,942,814 B2 | 5/2011 | Remijan et al. | |
| 8,016,839 B2 | 9/2011 | Wilk | |
| 8,038,602 B2 | 10/2011 | Gill et al. | |
| 8,046,057 B2 | 10/2011 | Clarke | |
| 8,052,609 B2 | 11/2011 | Harhen | |
| 8,142,346 B2 | 3/2012 | Shoroji et al. | |
| 8,170,319 B2 | 5/2012 | Shukla | |
| 8,277,411 B2 | 10/2012 | Gellman | |
| 8,317,689 B1 | 11/2012 | Remijan et al. | |
| 8,475,361 B2 * | 7/2013 | Barlow | A61B 1/0005 600/109 |
| 8,885,034 B2 | 11/2014 | Adair et al. | |
| 2001/0036015 A1 * | 11/2001 | Eguchi | 359/622 |
| 2001/0053873 A1 | 12/2001 | Schaaf et al. | |
| 2002/0007110 A1 | 1/2002 | Irion | |
| 2002/0072651 A1 * | 6/2002 | Vilos | A61B 1/12 600/105 |
| 2002/0087047 A1 | 7/2002 | Remijan et al. | |
| 2002/0177847 A1 | 11/2002 | Long | |
| 2003/0040668 A1 | 2/2003 | Kaneko et al. | |
| 2003/0120156 A1 | 6/2003 | Forrester et al. | |
| 2003/0181905 A1 | 9/2003 | Long | |
| 2003/0220574 A1 * | 11/2003 | Markus | A61B 1/05 600/466 |
| 2003/0233024 A1 | 12/2003 | Ando | |
| 2004/0102772 A1 | 5/2004 | Baxter et al. | |
| 2004/0162554 A1 | 8/2004 | Lee et al. | |
| 2004/0162572 A1 | 8/2004 | Sauer | |
| 2004/0215061 A1 * | 10/2004 | Kimmel et al. | 600/179 |
| 2005/0038317 A1 * | 2/2005 | Ratnakar | A61B 1/00105 600/101 |
| 2005/0090762 A1 | 4/2005 | Burbank et al. | |
| 2005/0113641 A1 | 5/2005 | Bala | |
| 2005/0154262 A1 * | 7/2005 | Banik et al. | 600/179 |
| 2005/0192532 A1 | 9/2005 | Kucklick et al. | |
| 2005/0197536 A1 | 9/2005 | Banik et al. | |
| 2005/0197658 A1 | 9/2005 | Platt | |
| 2005/0213267 A1 | 9/2005 | Azrai et al. | |
| 2005/0228228 A1 | 10/2005 | Boulais | |
| 2005/0234296 A1 | 10/2005 | Saadat et al. | |
| 2005/0277808 A1 * | 12/2005 | Sonnenschein et al. | 600/112 |
| 2006/0004258 A1 | 1/2006 | Sun et al. | |
| 2006/0004354 A1 | 1/2006 | Suslov | |
| 2006/0030861 A1 | 2/2006 | Simonson et al. | |
| 2006/0063973 A1 | 3/2006 | Makower et al. | |
| 2006/0069303 A1 * | 3/2006 | Couvillon, Jr. | 600/104 |
| 2006/0069313 A1 | 3/2006 | Couvillon, Jr. | |
| 2006/0084839 A1 | 4/2006 | Mourlas et al. | |
| 2006/0089633 A1 | 4/2006 | L. Bleich et al. | |
| 2006/0106282 A1 | 5/2006 | Bala | |
| 2006/0111613 A1 | 5/2006 | Boutillette et al. | |
| 2006/0149129 A1 * | 7/2006 | Watts et al. | 600/113 |
| 2006/0167340 A1 | 7/2006 | Pease et al. | |
| 2006/0173244 A1 | 8/2006 | Boulas et al. | |
| 2006/0190063 A1 | 8/2006 | Kanzius | |
| 2006/0206007 A1 | 9/2006 | Bala | |
| 2006/0206118 A1 | 9/2006 | Kim et al. | |
| 2006/0241648 A1 | 10/2006 | Bleich et al. | |
| 2006/0258951 A1 | 11/2006 | Bleich et al. | |
| 2006/0270904 A1 | 11/2006 | Kepferschmid et al. | |
| 2006/0276690 A1 | 12/2006 | Farris, III et al. | |
| 2006/0281972 A1 | 12/2006 | Uchimura et al. | |
| 2006/0287576 A1 | 12/2006 | Tsuji et al. | |
| 2006/0293562 A1 | 12/2006 | Uchimura et al. | |
| 2007/0038117 A1 | 2/2007 | Bala | |
| 2007/0049794 A1 | 3/2007 | Glassenberg et al. | |

(56) References Cited

U.S. PATENT DOCUMENTS

| | | |
|---|---|---|
| 2007/0060798 A1 | 3/2007 | Krupnik et al. |
| 2007/0071311 A1* | 3/2007 | Rovira-Mas ............ G06T 7/70 382/154 |
| 2007/0073109 A1 | 3/2007 | Irion |
| 2007/0075654 A1 | 4/2007 | Kishinevsky |
| 2007/0093689 A1 | 4/2007 | Steinberg |
| 2007/0115376 A1 | 5/2007 | Igarashi |
| 2007/0123888 A1 | 5/2007 | Bleich et al. |
| 2007/0129604 A1 | 6/2007 | Hatcher et al. |
| 2007/0129719 A1 | 6/2007 | Kendale et al. |
| 2007/0135874 A1 | 6/2007 | Bala |
| 2007/0161855 A1* | 7/2007 | Mikkaichi ............ A61B 1/0005 600/113 |
| 2007/0167678 A1 | 7/2007 | Moskowitz et al. |
| 2007/0167681 A1 | 7/2007 | Gill et al. |
| 2007/0179340 A1 | 8/2007 | Jorgensen |
| 2007/0213733 A1 | 9/2007 | Bleich et al. |
| 2007/0213734 A1 | 9/2007 | Bleich et al. |
| 2007/0213735 A1 | 9/2007 | Bleich et al. |
| 2007/0219412 A1 | 9/2007 | DiGiovanni et al. |
| 2007/0225556 A1 | 9/2007 | Oritz et al. |
| 2007/0232850 A1 | 10/2007 | Stokes et al. |
| 2007/0249904 A1 | 10/2007 | Amano et al. |
| 2007/0276183 A1 | 11/2007 | Melder |
| 2007/0287886 A1 | 12/2007 | Saadat |
| 2007/0293853 A1 | 12/2007 | Truckai et al. |
| 2008/0009747 A1 | 1/2008 | Saadat et al. |
| 2008/0033465 A1 | 2/2008 | Schmitz et al. |
| 2008/0051629 A1* | 2/2008 | Sugiyama et al. ............ 600/114 |
| 2008/0062429 A1 | 3/2008 | Liang et al. |
| 2008/0064925 A1 | 3/2008 | Gill et al. |
| 2008/0091064 A1 | 4/2008 | Laser |
| 2008/0103504 A1 | 5/2008 | Schmitz et al. |
| 2008/0108869 A1 | 5/2008 | Sanders et al. |
| 2008/0147018 A1* | 6/2008 | Squilla et al. ................ 604/264 |
| 2008/0161809 A1 | 7/2008 | Schmitz et al. |
| 2008/0051812 A1 | 8/2008 | Schmitz et al. |
| 2008/0200758 A1 | 8/2008 | Orbay et al. |
| 2008/0207992 A1 | 8/2008 | Scheller et al. |
| 2008/0207996 A1 | 8/2008 | Tsai |
| 2008/0214896 A1 | 9/2008 | Krupa et al. |
| 2008/0262302 A1* | 10/2008 | Azarbarzin ........ A61B 1/00052 600/114 |
| 2008/0287961 A1* | 11/2008 | Miyamoto et al. ........... 606/127 |
| 2008/0300462 A1 | 12/2008 | Intoccia et al. |
| 2009/0043165 A1 | 2/2009 | Kucklick et al. |
| 2009/0076329 A1 | 3/2009 | Su et al. |
| 2009/0253967 A1 | 10/2009 | Gill et al. |
| 2009/0264706 A1 | 10/2009 | Bala |
| 2010/0016855 A1 | 1/2010 | Ramstein et al. |
| 2010/0022824 A1* | 1/2010 | Cybulski et al. ............. 600/104 |
| 2010/0056862 A1 | 3/2010 | Bakos |
| 2010/0063352 A1 | 3/2010 | Matsuura |
| 2010/0063356 A1* | 3/2010 | Smith ........................... 600/114 |
| 2010/0087798 A1 | 4/2010 | Adams et al. |
| 2010/0094231 A1 | 4/2010 | Bleich et al. |
| 2010/0121139 A1 | 5/2010 | OuYang et al. |
| 2010/0121155 A1 | 5/2010 | OuYang et al. |
| 2010/0165335 A1 | 7/2010 | Tearney |
| 2010/0165336 A1 | 7/2010 | Terney |
| 2010/0217080 A1 | 8/2010 | Cheung et al. |
| 2010/0256446 A1* | 10/2010 | Raju ............................. 600/114 |
| 2010/0274081 A1 | 10/2010 | Okoniewski |
| 2010/0284580 A1 | 11/2010 | OuYang et al. |
| 2010/0286477 A1 | 11/2010 | OuYang et al. |
| 2011/0009694 A1 | 1/2011 | Schultz et al. |
| 2011/0034769 A1 | 2/2011 | Adair et al. |
| 2011/0227509 A1 | 9/2011 | Saleh |
| 2011/0263933 A1 | 10/2011 | Schaaf |
| 2011/0263983 A1 | 10/2011 | Peszynski |
| 2011/0276113 A1 | 11/2011 | Cybulski |
| 2012/0071721 A1 | 3/2012 | Remijan et al. |
| 2012/0088968 A1 | 4/2012 | Gambhir et al. |
| 2012/0095458 A1 | 4/2012 | Cybulski et al. |
| 2012/0241188 A1 | 9/2012 | Power et al. |
| 2012/0265009 A1 | 10/2012 | OuYang et al. |
| 2013/0046142 A1 | 2/2013 | Remijan et al. |
| 2013/0144122 A1 | 6/2013 | Adair et al. |
| 2013/0296648 A1 | 11/2013 | OuYang et al. |
| 2013/0303846 A1 | 11/2013 | Cybulski et al. |
| 2015/0313634 A1 | 11/2015 | Gross et al. |
| 2016/0045224 A1 | 2/2016 | Hendershot, III |
| 2016/0296108 A1 | 10/2016 | Kienzle et al. |
| 2017/0042408 A1 | 2/2017 | Washburn et al. |
| 2017/0042573 A1 | 2/2017 | Savvouras et al. |
| 2017/0086666 A1 | 3/2017 | Kienzle et al. |

FOREIGN PATENT DOCUMENTS

| | | |
|---|---|---|
| CN | 1612708 A | 5/2005 |
| CN | 1779836 A | 5/2006 |
| CN | 101040775 A | 9/2007 |
| CN | 103961177 A | 8/2014 |
| CN | 104367296 A | 2/2015 |
| CN | 106455907 A | 2/2017 |
| EP | 1252859 A2 | 10/2002 |
| EP | 2317931 A2 | 5/2011 |
| EP | 2335550 | 6/2011 |
| EP | 2451338 A2 | 5/2012 |
| EP | 3094231 | 11/2016 |
| GB | 2431539 A | 4/2007 |
| JP | H1033462 A | 2/1998 |
| JP | 2001-161630 | 6/2001 |
| WO | WO 00/09001 | 2/2000 |
| WO | WO 2006/107877 | 10/2006 |
| WO | WO 2007/106740 | 9/2007 |
| WO | WO 2008/016927 | 2/2008 |
| WO | WO 2008/094436 | 8/2008 |
| WO | WO 2008/094439 | 8/2008 |
| WO | WO 2008/094444 | 8/2008 |
| WO | WO 2008/098251 | 8/2008 |
| WO | WO 2010/011781 | 1/2010 |
| WO | WO 2011/006052 | 1/2011 |
| WO | WO 2014/137530 | 9/2014 |
| WO | WO 2015/106288 | 7/2015 |
| WO | WO 2016/130844 | 8/2016 |
| WO | WO 2017/027749 | 2/2017 |
| WO | WO 2017/161777 | 9/2017 |

OTHER PUBLICATIONS

U.S. Appl. No. 14/526,289, filed Oct. 28, 2014, Cybulski.
U.S. Appl. No. 14/596,093, filed Jan. 13, 2015, Kienzle et al.
U.S. Appl. No. 14/622,680, filed Feb. 13, 2015, OuYang et al.
Keller C.A., Hinerman, R., Singh, A., Alvarez, F., "The Use of Endoscopic Argon Plasma Coagulation in Airway Complications After Solid Organ Transplantation," *Chest*, 2001, vol. 119, No. 6, pp. 1968-1975.
U.S. Appl. No. 15/234,999, filed Aug. 11, 2016, Washburn et al.
U.S. Appl. No. 15/258,968, filed Sep. 7, 2016, Kienzle et al.
U.S. Appl. No. 15/461,994, filed Mar. 17, 2017, Washburn et al.

* cited by examiner

TISSUE VISUALIZATION AND MODIFICATION DEVICE

CROSS-REFERENCE TO RELATED APPLICATIONS

This application is continuation of U.S. patent application Ser. No. 12/269,770, filed Nov. 12, 2008, the entirety of which is hereby incorporated by reference herein.

BACKGROUND OF THE INVENTION

Many pathological conditions in the human body may be caused by enlargement, movement, displacement and/or a variety of other changes of bodily tissue, causing the tissue to press against (or "impinge on") one or more otherwise normal tissues or organs. For example, a cancerous tumor may press against an adjacent organ and adversely affect the functioning and/or the health of that organ. In other cases, bony growths (or "bone spurs"), arthritic changes in bone and/or soft tissue, redundant soft tissue, or other hypertrophic bone or soft tissue conditions may impinge on nearby nerve and/or vascular tissues and compromise functioning of one or more nerves, reduce blood flow through a blood vessel, or both. Other examples of tissues which may grow or move to press against adjacent tissues include ligaments, tendons, cysts, cartilage, scar tissue, blood vessels, adipose tissue, tumor, hematoma, and inflammatory tissue.

The intervertebral disc 10 is composed of a thick outer ring of cartilage (annulus fibrosus, 12) and an inner gel-like substance (nucleus pulposus 14). A three-dimensional view of an intervertebral disc is provided in FIG. 1. The annulus 10 contains collagen fibers that form concentric lamellae 16 that surround the nucleus and insert into the endplates of the adjacent vertebral bodies. The nucleus pulposus 14 comprises proteoglycans entrapped by a network of collagen and elastin fibers which has the capacity to bind water. When healthy, the intervertebral disc keeps the spine flexible and serves as a shock absorber by allowing the body to accept and dissipate loads across multiple levels in the spine.

With respect to the spine and intervertebral discs, a variety of medical conditions can occur in which it is desirable to ultimately surgically remove at least some of if not all of an intervertebral disc. As such, a variety of different conditions exist where partial or total disc removal is desirable.

One such condition is disc herniation. Over time, the nucleus pulposus becomes less fluid and more viscous as a result of age, normal wear and tear, and damage caused from an injury. The proteoglycan and water from within the nucleus decreases which in turn results in the nucleus drying out and becoming smaller and compressed. Additionally, the annulus tends to thicken, desiccate, and become more rigid, lessening its ability to elastically deform under load and making it susceptible to disc fissures.

A fissure occurs when the fibrous components of the annulus become separated in particular areas, creating a tear within the annulus. The most common type of fissure is a radial fissure in which the tear is perpendicular to the direction of the fibers. A fissure associated with disc herniation generally falls into three types of categories: 1) contained disc herniation (also known as contained disc protrusion); 2) extruded disc herniation; and 3) sequestered disc herniation (also known as a free fragment.) In a contained herniation, a portion of the disc protrudes or bulges from a normal boundary of the disc but does not breach the outer annulus fibrosis. In an extruded herniation, the annulus is disrupted and a segment of the nucleus protrudes/extrudes from the disc. However, in this condition, the nucleus within the disc remains contiguous with the extruded fragment. With a sequestered disc herniation, a nucleus fragment separates from the nucleus and disc.

As the posterior and posterolateral portions of the annulus are most susceptible to herniation, in many instances, the nucleus pulposus progresses into the fissure from the nucleus in a posteriorly or posterolateral direction. Additionally, biochemicals contained within the nucleus pulposus may escape through the annulus causing inflammation and irritating adjacent nerves. Symptoms of a herniated disc generally include sharp back or neck pain which radiates into the extremities, numbness, muscle weakness, and in late stages, paralysis, muscle atrophy and bladder and bowel incontinence.

Conservative therapy is the first line of treating a herniated disc which includes bed rest, medications to reduce inflammation and pain, physical therapy, patient education on proper body mechanics and weight control.

If conservative therapy offers no improvement then surgery is recommended. Open discectomy is the most common surgical treatment for ruptured or herniated discs. The procedure involves an incision in the skin over the spine to remove the herniated disc material so it no longer presses on the nerves and spinal cord. Before the disc material is removed, some of the bone from the affected vertebra may be removed using a laminotomy or laminectomy to allow the surgeon to better see the area. As an alternative to open surgery, minimally invasive techniques have been rapidly replacing open surgery in treating herniated discs. Minimally invasive surgery utilizes small skin incisions, thereby minimizing the damaging effects of large muscle retraction and offering rapid recovery, less post-operative pain and small incisional scars.

SUMMARY OF THE INVENTION

Aspects of the invention include minimally invasive imaging system. Systems according to embodiments of the invention include: an access device having a proximal end and distal end and an internal passageway extending from the proximal to distal end; and an elongated member dimensioned to be slidably moved through the internal passageway of the access device and having a proximal and distal end. In the systems of the invention, at least one of multiple visualization elements and multiple illumination elements are positioned among the distal ends of the access device and the elongated member. Also provided are methods of using the systems in imaging applications, as well as kits for performing the methods.

DETAILED DESCRIPTION OF THE PREFERRED EMBODIMENT

Figure 1:
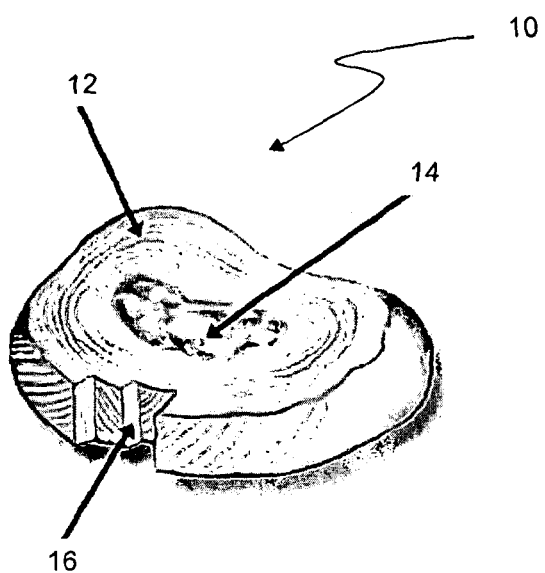
FIG. 1 provides a three-dimensional view of an intervertebral disc according to one embodiment of the invention.

Aspects of the invention include minimally invasive imaging system. Systems according to embodiments of the invention include: an access device having a proximal end and distal end and an internal passageway extending from the proximal to distal end; and an elongated member dimensioned to be slidably moved through the internal passageway of the access device and having a proximal end and a distal end. In the systems of the invention, at least one of multiple visualization elements and multiple illumination elements are positioned among the distal ends of the access device and the elongated member. Also provided are methods of using the systems in imaging applications, as well as kits for performing the methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, embodiments of the minimally invasive imaging systems and components thereof are reviewed first in greater detail, followed by a review of embodiments of methods of using the devices.

Minimally Invasive Imaging Systems

As summarized above, aspects of the invention include minimally invasive imaging systems. The imaging systems of the invention are minimally invasive, such that they may be introduced to an internal target site of a patient, e.g., a spinal location that is near or inside of an intervertebral disc, through a minimal incision, e.g., one that is less than the size of an incision employed for an access device having a outer diameter of 20 mm or larger, e.g., less than 75% the size of such an incision, such as less than 50% of the size of such an incision, or smaller.

Imaging systems of the invention include both an access device and an elongate member. The access device is a device having a proximal end and a distal end and an internal passageway extending from the proximal to distal end. Similarly, the elongated member has a proximal end and a distal end and is dimensioned to be slidably moved through the internal passageway of the access device. Aspects of the invention include at least one of multiple visualization elements and multiple illumination elements that are positioned among the distal ends of the access device and the elongated member.

Access devices of the invention are elongated elements having an internal passageway that are configured to provide access to a user (e.g., a health care professional, such as a surgeon) from an extra-corporeal location to an internal target tissue site, e.g., a location near or in the spine or component thereof, e.g., near or in an intervertebral disc, inside of the disc, etc., through a minimally invasive incision. Access devices of the invention may be cannulas, components of retractor tube systems, etc. As the access devices are elongate, they have a length that is 1.5 times or longer than their width, such as 2 times or longer than their width, including 5 or even 10 times or longer than their width, e.g., 20 times longer than its width, 30 times longer than its width, or longer.

Where the access devices are configured to provide access through a minimally invasive incision, the longest cross-sectional outer dimension of the access devices (for example, the outer diameter of a tube shaped access device, including wall thickness of the access device, which may be a port or cannula in some instances) ranges in certain instances from 5 mm to 50 mm, such as 10 to 20 mm. With respect to the internal passageway, this passage is dimensioned to provide passage of the tools, e.g., imaging devices, tissue modifiers, etc., from an extra-corporeal site to the internal target tissue location. In certain embodiments, the longest cross-sectional dimension of the internal passageway, e.g., the inner diameter of a tubular shaped access device, ranges in length from 5 to 30 mm, such as 5 to 25 mm, including 5 to 20 mm, e.g., 7 to 18 mm. Where desired, the access devices are sufficiently rigid to maintain mechanical separation of tissue, e.g., muscle, and may be fabricated from any convenient material. Materials of interest from which the access devices may be fabricated include, but are not limited to: metals, such as stainless steel and other medical grade metallic materials, plastics, and the like.

The systems of the invention further include an elongate member having a proximal and distal end, where the elongate member is dimensioned to be slidably moved through the internal passageway of the access device. As this component of the systems is elongate, it has a length that is 1.5 times or longer than its width, such as 2 times or longer than its width, including 5 or even 10 times or longer than its width, e.g., 20 times longer than its width, 30 times longer than its width, or longer. When designed for use in IVD procedures, the elongate member is dimensioned to access an intervertebral disc. By "dimensioned to access an intervertebral disc" is meant that at least the distal end of the device has a longest cross-sectional dimension that is 10 mm or less, such as 8 mm or less and including 7 mm or less, where in certain embodiments the longest cross-sectional dimension has a length ranging from 5 to 10 mm, such as 6 to 9 mm, and including 6 to 8 mm. The elongate member may be solid or include one or more lumens, such that it may be viewed as a catheter. The term "catheter" is employed in its conventional sense to refer to a hollow, flexible or semi-rigid tube configured to be inserted into a body. Catheters of the invention may include a single lumen, or two or more lumens, e.g., three or more lumens, etc, as desired. Depending on the particular embodiment, the elongate members may be flexible or rigid, and may be fabricated from any convenient material.

Figure 3:
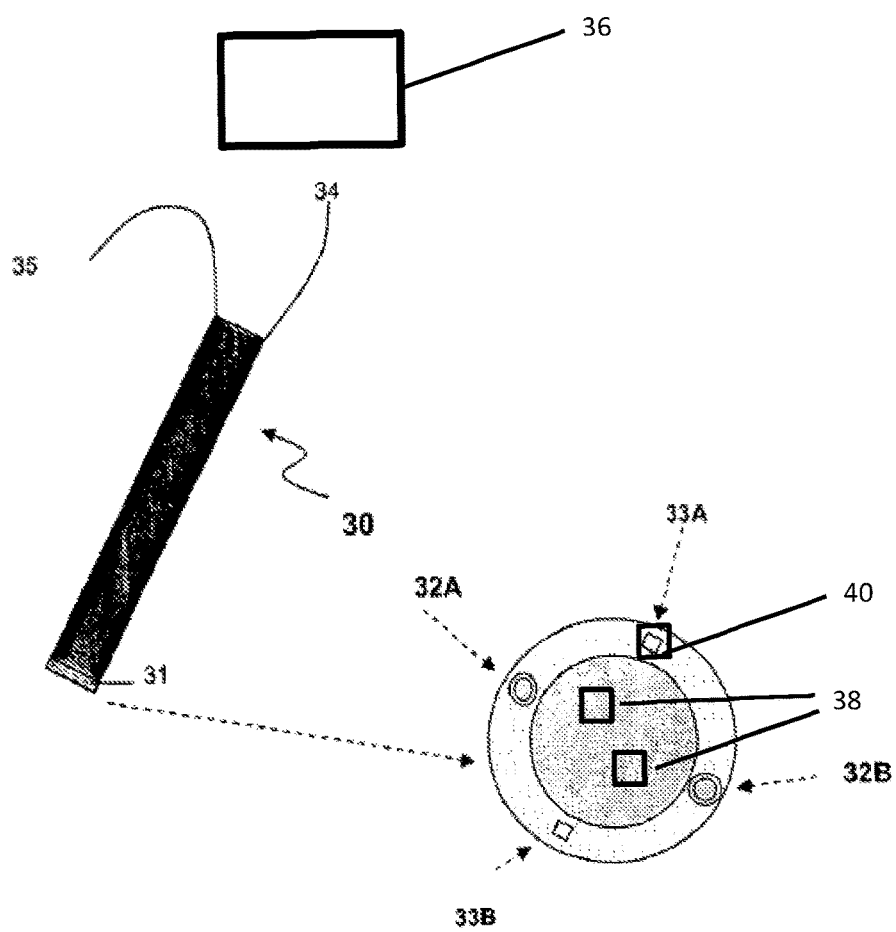
FIG. 3 provides a view of an access device according to an embodiment of the invention.

As summarized above, aspects of the invention include at least one of multiple visualization elements and multiple illumination elements that are positioned among the distal ends of the access device and the elongated member. By "at least one of multiple visualization elements and multiple illumination elements" is meant that, over all, the system includes two or more visualization elements and/or two or more illumination elements that are located among the distal ends of access device and elongated member. Accordingly, embodiments of the systems include those systems where two or more visualization elements 38, examples of which are depicted in FIG. 3, are located at the distal end of the elongated member. Embodiments of the systems also include those systems where one visualization element is located at the distal end of the elongated member and another visualization element is located at the distal end of the access device. Furthermore, embodiments of the systems include those systems where two or more visualization elements are located at the distal end of the access device.

Similarly, with respect to the illumination elements, embodiments of the systems include those systems where two or more illumination elements are located at the distal end of the elongated member. Embodiments of the systems also include those systems where one illumination element is located at the distal end of the elongated member and another illumination element is located at the distal end of the access device. Furthermore, embodiments of the systems include those systems where two or more illumination elements are located at the distal end of the access device.

Accordingly, the phrase "among the distal ends of the access device and elongated member" means that between the two distal ends, there is positioned at least one of multiple visualization elements and multiple illumination elements. By "located among the distal ends" is meant that the item of interest (e.g., the visualization element, the illumination element) is present at the distal end of the elongate member and/or access device, or near the distal end of the elongate member and/or access device, e.g., within 10 mm or closer to the distal end, such as within 5 mm or closer to the distal end and including within 3 mm or closer to the distal end.

Of interest as visualization elements are imaging sensors. Imaging sensors of interest are miniature in size so as to be positionable at the distal end of the elongate member or the access device. Miniature imaging sensors of interest are those that, when integrated at the distal end of an elongated structure along with an illumination source, e.g., such as an LED as reviewed below, can be positioned on a probe having a longest cross section dimension of 6 mm or less, such as 5 mm or less, including 4 mm or less, and even 3 mm or less. In certain embodiments, the miniature imaging sensors have a longest cross-section dimension (such as a diagonal dimension) of 5 mm or less, such 3 mm or less, where in certain instances the sensors may have a longest cross-sectional dimension ranging from 2 to 3 mm. In certain embodiments, the miniature imaging sensors have a cross-sectional area that is sufficiently small for its intended use and yet retain a sufficiently high matrix resolution. Certain imaging sensors of the invention have a cross-sectional area (i.e. an x-y dimension, also known as packaged chip size) that is 2 mm.times.2 mm or less, such as 1.8 mm.times.1.8 mm or less, and yet have a matrix resolution of 400.times.400 or greater, such as 640.times.480 or greater. In some instances, the imaging sensors have a sensitivity that is 500 mV/Lux-sec or greater, such as 700 mV/Lux-Sec or greater, including 1000 mV/Lux-Sec or greater, where in some instances the sensitivity of the sensor is 2000 mV/Lux-Sec or greater, such as 3000 mV/Lux-Sec or greater. The imaging sensors of interest are those that include a photosensitive component, e.g., array of photosensitive elements, coupled to an integrated circuit, where the integrated circuit is configured to obtain and integrate the signals from the photosensitive array and output the analog data to a backend processor. The image sensors of interest may be viewed as integrated circuit image sensors, and include complementary metal-oxide-semiconductor (CMOS) sensors and charge-coupled device (CCD) sensors. The image sensors may further include a lens positioned relative to the photosensitive component so as to focus images on the photosensitive component. A signal conductor may be present to connect the image sensor at the distal and to a device at the proximal end of the elongate member, e.g., in the form of one or more wires running along the length of the elongate member from the distal to the proximal end. Imaging sensors of interest include, but are not limited to, those obtainable from: OminVision Technologies Inc., Sony Corporation, Cypress Semiconductors. The imaging sensors may be integrated with the component of interest, e.g., the access device or the elongated structure. As the imaging sensor(s) is integrated at the distal end of the component, it cannot be removed from the remainder of the component without significantly compromising the structure of component. As such, the integrated visualization element is not readily removable from the remainder of the component, such that the visualization element and remainder of the component form an inter-related whole.

While any convenient imaging sensor may be employed in devices of the invention, in certain instances the imaging sensor is a CMOS sensor. Of interest as CMOS sensors are the OmniPixel line of CMOS sensors available from OmniVision (Sunnyvale, Calif.), including the OmniPixel, OmniPixel2, OmniPixel3, OmniPixel3-HS and OmniBSI lines of CMOS sensors. These sensors may be either frontside or backside illumination sensors, and have sufficiently small dimensions while maintaining sufficient functionality to be positioned at the distal end of the minimally invasive devices of the invention. Aspects of these sensors are further described in one or more the following U.S. patents, the disclosures of which are herein incorporated by reference: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

A variety of different types of lights sources may be employed as illumination elements, so long as their dimensions are such that they can be positioned at the distal end of the access device and/or elongated member. The light sources may be integrated with a given component (e.g., access device, elongated member) such that they are configured relative to the component such that the light source element cannot be removed from the remainder of the component without significantly compromising the structure of the component. As such, the integrated illumination element of these embodiments is not readily removable from the remainder of the component, such that the illumination element and remainder of the component form an inter-related whole. The light sources may be light emitting diodes configured to emit light of the desired wavelength range, or optical conveyance elements, e.g., optical fibers, configured to convey light of the desired wavelength range from a location other than the distal end of the elongate member, e.g., a location at the proximal end of the elongate member, to the distal end of the elongate member. As with the image sensors, the light sources may include a conductive element, e.g., wire, optical fiber, which runs the length of the elongate member to provide for control of the light sources from a location outside the body, e.g., an extracorporeal control device. Where desired, the light sources may include a diffusion element 40, an example of which is depicted in FIG. 3, to provide for uniform illumination of the target tissue site. Any convenient diffusion element may be employed, including but not limited to a translucent cover or layer (fabricated from any convenient translucent material) through which light from the light source passes and is thus diffused. In those embodiments of the invention where the system includes two or more illumination elements, the illumination elements may emit light of the same wavelength or they may be spectrally distinct light sources, where by "spectrally distinct" is meant that the light sources emit light at wavelengths that do not substantially overlap, such as white light and infra-red light, such as the spectrally distinct light sources described in copending U.S. application Ser. No. 12/269,772 titled "Minimally Invasive Imaging Device" filed on even date herewith; the disclosure of which is herein incorporated by reference. In certain embodiments, the elongate member of the system further includes a tissue modifier. Tissue modifiers are components or sub-devices that interact with tissue in some manner to modify the tissue in a desired way. The term modify is used broadly to refer to changing in some way, including cutting the tissue, ablating the tissue, delivering an agent(s) to the tissue, freezing the tissue, etc. As such, of interest as tissue modifiers are tissue cutters, tissue ablators, tissue freezing/heating elements, agent delivery devices, etc. Tissue cutters of interest include, but are not limited to: blades, liquid jet devices, lasers and the like. Tissue ablators of interest include, but are not limited to ablation devices, such as devices for delivery ultrasonic energy (e.g., as employed in ultrasonic ablation), devices for delivering plasma energy, devices for delivery radiofrequency (RF) energy, devices for delivering microwave energy, etc. Energy transfer devices of interest include, but are not limited to: devices for modulating the temperature of tissue, e.g., freezing or heating devices, etc.

In certain embodiments, the elongated member may further include one or more lumens that run at least the substantial length of the device, e.g., for performing a variety of different functions. In certain embodiments where it is desired to flush (i.e., wash) the location of the target tissue at the distal end of the elongate member (e.g., to remove cut tissue from the location, etc.), the elongated member may include both an irrigation and aspiration lumen. During use, the irrigation lumen is operatively connected to a fluid source (e.g., physiologically acceptable fluid, such as saline) at the proximal end of the device, where the fluid source is configured to introduce fluid into the lumen under positive pressure, e.g., at a pressure ranging from 0 to 500 mm Hg, so that fluid is conveyed along the irrigation lumen and out the distal end. While the dimensions of the irrigating lumen may vary, in certain embodiments the longest cross-sectional dimension of the irrigation lumen ranges from 1 to 3 mm. During use, the aspiration lumen is operatively connected to a source of negative pressure (e.g., vacuum source) at the proximal end of the device, where the negative pressure source is configured to draw fluid from the tissue location at the distal end into the irrigation lumen under positive pressure, e.g., at a pressure ranging from 50 to 600 mm Hg, so that fluid is removed from the tissue site and conveyed along the irrigation lumen and out the proximal end, e.g., into a waste reservoir. While the dimensions of the aspiration lumen may vary, in certain embodiments the longest cross-sectional dimension of the aspiration lumen ranges from 1 to 4 mm, such as 1 to 3 mm.

In certain embodiments, the systems of the invention are used in conjunction with a controller 36, an example of which is depicted in FIG. 3, configured to control illumination of the illumination elements and/or capture of images (e.g., as still imaged or video output) from the image sensors. This controller may take a variety of different formats, including hardware, software and combinations thereof. The controller may be physically located relative to the elongated member and/or access device at any convenient location, where the controller may be present at the distal end of the system components, at some point between the distal and proximal ends or at the proximal ends of the system components, as desired. In certain embodiments, the controller may be distinct from the system components, i.e., access device and elongated member, such the access device and/or elongated member includes a controller interface for operatively coupling to the distinct controller, or the controller may be integral with the device.

Figure 2:
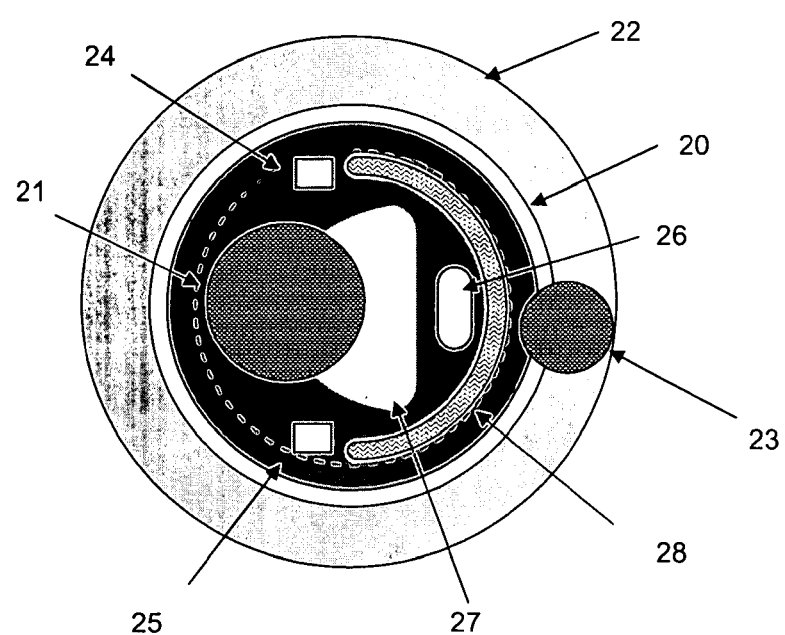
FIG. 2 provides a view of a cross section of the proximal end of a surgical device configured to remove the nucleus pulposus of an intervertebral disc (IVD) according to an embodiment of the invention.

FIG. 2 provides a cross-sectional view of the distal ends of the elongated member and access device of a system according to one embodiment of the invention, where the system is configured to be employed in the surgical removal of the nucleus pulposus of an intervertebral disc. In FIG. 2, distal end of elongated member 20 (in this embodiment a catheter) includes first imaging sensor 21 while distal end of access device 22 includes a second imaging sensor 23. Also shown at the distal end of elongated member 20 are first and second LEDs, 24 and 25. Also shown is an irrigation lumen 26 and aspiration lumen 27. In addition, the device includes a tissue modifier in the form of a dissection electrode 28. In the system shown in FIG. 2, the first imaging sensor 21 provides visualization of the target tissue site. The second imaging sensor 23 is positioned on the access device (although it could be positioned at a variety of locations on the access device or the elongated member). The orientation of second imaging sensor 23 is such that imaging sensor 23 provides imaged data of the elongated member, e.g., of the distal end of the elongated member during placement, etc. Any convenient positioning as use may be achieved.

FIG. 3 provides different views of an access device according to an embodiment of the invention. As shown in FIG. 3, access device 30 includes a distal end 31. Positioned at distal end 31 are two cameras 32A and 32B and two illumination sources, e.g., LEDs or light fibers, 33A and 33B. Running the length of the access device and exiting the proximal end are wires 34 and 35 for provide power and control to the cameras and visualization elements, e.g., via coupling to a control device.

Figure 4:
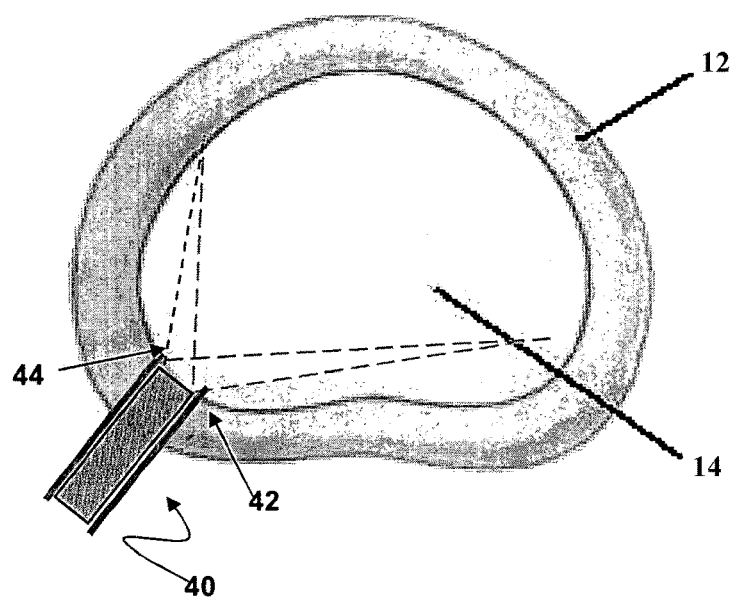
FIG. 4 illustrates a visualization device according to one embodiment of the invention viewing the nucleus pulposus of an intervertebral disc through an access port provided by a access device, such as a retractor tube.
Figure 5:
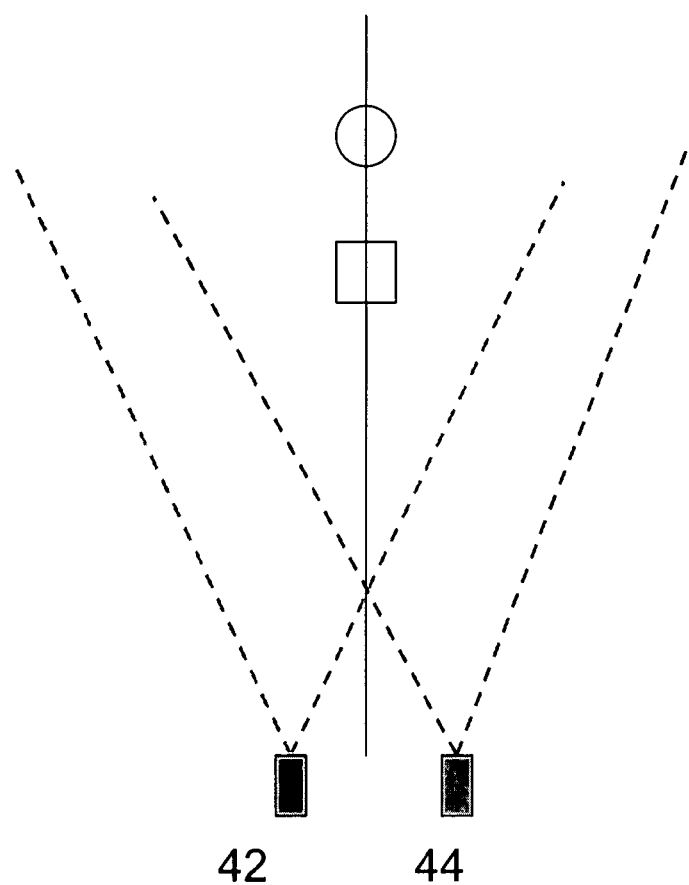
FIG. 5 provides a diagrammatic view of the positioning of two imaging sensors to provide a stereoscopic view of an internal target tissue site.

The multiple visualization and/or illumination elements of the devices may be positioned relative to each other in a variety of different ways. By selective positioning of these elements coupled, as desired, with specific image data processing techniques, unique views of the target tissue site may be obtained. For example, as illustrated in FIG. 4, two cameras 42 and 44 may be positioned in the same cross-section of the distal end of the imaging device. Image data from the two cameras can, in such an embodiment, be combined to obtain a panoramic view of the target tissue site, in this case the nucleus pulposus. This configuration also allows one to obtain a stereoscopic view of the target tissue site, as illustrated in FIG. 5, e.g., by synchronizing the image data from the two cameras. As illustrated in FIG. 5, by image processing the depth of the circle object can be distinguished from the square object. For embodiments where stereovision is desired, the ratio of object distance (i.e., distance of object of interest from the camera) to stereo baseline (i.e., camera to camera distance) may vary, and in certain instances ranges from 10 to 30, such as 15 to 25, e.g., 20 (e.g., where the object depth is 20 mm and the two cameras are 1 mm apart).

Placement of the visualization elements in different cross sections of the devices and/or on different devices can also provide for advantages in imaging. For example, FIG. 2 provides an illustration of a distal end of a system made up of a catheter visualization device slidably positioned within an internal passageway of an access device, such as a retractor tube. In the embodiment depicted in FIG. 2, the primary camera 21 is on the cross section of the catheter, and the secondary camera 23 is on the wall of the access device. Both cameras can be arranged to have certain orientations, as desired, such as forward viewing or angled or side viewing. Illuminations can also be arranged such that different views of the same object can be revealed. For example, the light source can be somewhat collimated or focused in a certain direction to give a better view of the surgical blades, electrodes or the local tissue appearance.

The devices or components thereof may be configured for one time use (i.e., disposable) or re-usable, e.g., where the components are configured to be used two or more times before disposal, e.g., where the device components are sterilizable.

Methods

Aspects of the invention further include methods of imaging an internal tissue site with imaging devices of the invention. A variety of internal tissue sites can be imaged with devices of the invention. In certain embodiments, the methods are methods of imaging an intervertebral disc in a minimally invasive manner. For ease of description, the methods are now primarily described further in terms of imaging IVD target tissue sites. However, the invention is not so limited, as the devices may be used to image a variety of distinct target tissue sites.

With respect to imaging an intervertebral disc or portion thereof, e.g., exterior of the disc, nucleus pulposus, etc., embodiments of such methods include positioning a distal end of a minimally invasive intervertebral disc imaging device of the invention in viewing relationship to an intervertebral disc or portion of there, e.g., nucleus pulposus, internal site of nucleus pulposus, etc. By viewing relationship is meant that the distal end is positioned within 40 mm, such as within 10 mm, of the target tissue site of interest. Positioning the distal end in viewing device in relation to the desired target tissue may be accomplished using any convenient approach, including through use of an access device, such as a cannula or retractor tube, which may or may not be fitted with a trocar, as desired. Following positioning of the distal end of the imaging device in viewing relationship to the target tissue, the target tissue, e.g., intervertebral disc or portion thereof, is imaged through use of the illumination and visualization elements to obtain image data. Image data obtained according to the methods of the invention is output to a user in the form of an image, e.g., using a monitor or other convenient medium as a display means. In certain embodiments, the image is a still image, while in other embodiments the image may be a video.

In certain embodiments, the methods include a step of tissue modification in addition to the tissue viewing. For example, the methods may include a step of tissue removal, e.g., using a combination of tissue cutting and irrigation or flushing. For example, the methods may include cutting a least a portion of the tissue and then removing the cut tissue from the site, e.g., by flushing at least a portion of the imaged tissue location using a fluid introduce by an irrigation lumen and removed by an aspiration lumen.

FIG. 4 provides a view of one embodiment of a method of visualizing an intervertebral disc. In the embodiment illustrated in FIG. 4, an access device, e.g., cannula, trocar, etc. is employed to provide access of the device to the internal body site, e.g., via a minimally sized incision. FIG. 4 shows a visualization device according to an embodiment of the invention viewing the nucleus pulposus of an intervertebral disc through an access port provided by an access device, such as a cannula. In FIG. 4, the visualization elements are positioned at the distal end of a catheter member, and are located in the same cross-sectional plane. Image data from the two visualization elements may be obtained and processed to provide for an enhanced field of view, e.g., a panoramic view, where the enhanced field of view may be one that is wider than the view obtained from a signal visualization element and/or provide for stereoscopic view, as illustrated in FIG. 5.

Figure 6:
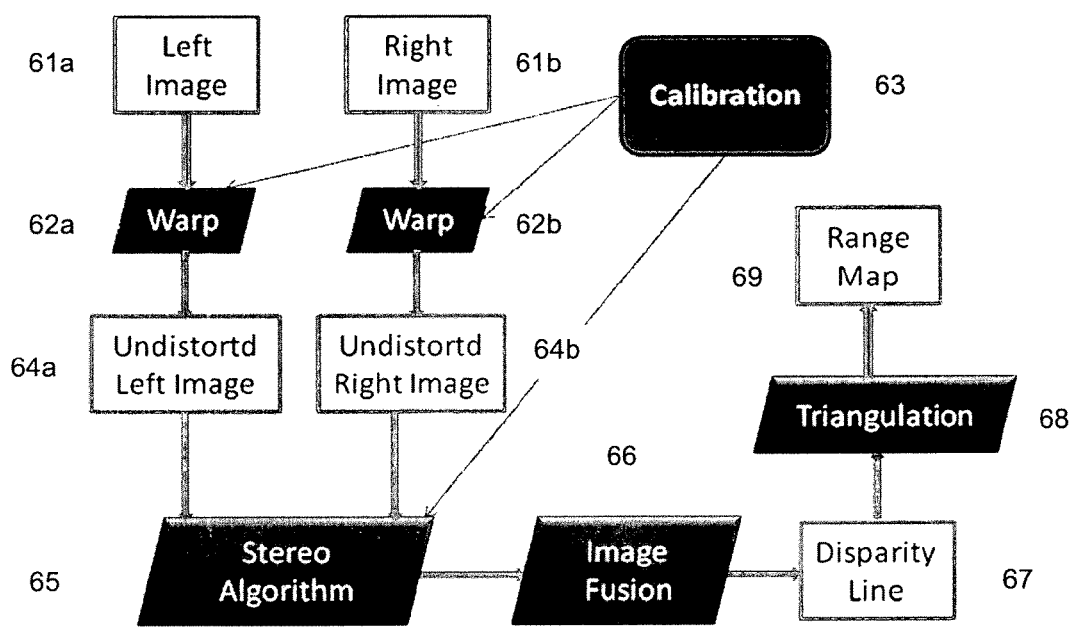
FIG. 6 provides a schematic representation of the operational framework of a processor that may be present in a device according to embodiments of the invention.

FIG. 6 provides a flow chart representation of a stereoscopic image processing algorithm according to an embodiment of the invention, where the algorithm is configured to derived depth or "range" map on a two-dimensional scene.

In the process depicted in FIG. 6, left and right images 61a and 61b obtained by two distinct visualization elements, e.g., sensors 42 and 44 as depicted in FIG. 5, are first warped as shown at 62a and 62b via calibration element 63 to remove lens distortion. The resultant undistorted left and right images 64a and 64b are then processed with stereo and image fusion algorithms 65 and 66 to derive a disparity line 67. Finally, triangulation computations 68 are applied to derive range data. The range (or depth) map 69 can be overlay on the image display, as desired.

Methods of invention may find use in any convenient application, including diagnostic and therapeutic applications. Specific applications of interest include, but are not limited to, intervertebral disc diagnostic and therapeutic applications. For example, methods of the invention include diagnostic applications, where a disc is viewed to determine any problems with the disc, if present. Methods of the invention also include treatment methods, e.g., where a disc is modified in some manner to treat and existing medical condition. Treatment methods of interest include, but are not limited to: annulotomy, nucleotomy, discectomy, annulus replacement, nucleus replacement, and decompression due to a bulging or extruded disc. Additional methods in which the imaging devices find use include those described in United States Published Application No. 20080255563.

Methods and devices of the invention may be employed with a variety of subjects. In certain embodiments, the subject is an animal, where in certain embodiments the animal is a "mammal" or "mammalian." The terms mammal and mammalian are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects (i.e., patients) are humans.

Kits

Also provided are kits for use in practicing the subject methods, where the kits may include one or more of the above devices, and/or components of the subject systems, as described above. As such, a kit may include a visualization device and an access device, e.g., a cannula configured to be employed with the visualization device. The kit may further include other components, e.g., guidewires, stylets, etc., which may find use in practicing the subject methods. Various components may be packaged as desired, e.g., together or separately.

In addition to above mentioned components, the subject kits may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Computer Readable Storage Media

Also of interest is programming that is configured for operating a visualization device according to methods of invention, where the programming is recorded on physical computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a storage medium having instructions for operating a minimally invasive in accordance with the invention.

Programming of the invention includes instructions for operating a device of the invention, such that upon execution by the programming, the executed instructions result in execution of the imaging device to: illuminate a target tissue site, such as an intervertebral disc or portion thereof; and capture one or more image frames of the illuminated target tissue site with the imaging sensor.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A tissue visualization and modification device, comprising:
    a rigid access body extending along a longitudinal axis between a proximal end and a distal end, the access body comprising an internal passageway extending from the proximal end to the distal end, wherein the access body comprises an access body imaging sensor positioned on the distal end of the access body; and
    an elongated member slidably positioned within the rigid access body, the elongated member comprising, when viewed substantially along the longitudinal axis:
        a dissection electrode in the shape of a semicircle, the dissection electrode configured to remove a tissue,
        an irrigation channel positioned within the semicircle,
        a first illumination element positioned adjacent a first tip of the semicircle and a second illumination element positioned adjacent a second tip of the semicircle,
        an aspiration channel positioned partially within the semicircle and adjacent the irrigation channel, and
        an elongated member imaging sensor positioned adjacent the aspiration channel,
    wherein the access body imaging sensor protrudes inward beyond an inner wall of the access body into the internal passageway.

2. The tissue visualization and modification device of claim 1, wherein the access body imaging sensor is configured to view a distal end of the elongated member.

3. The tissue visualization and modification device of claim 1, wherein the first illumination element extends the length of the elongated member, the first illumination element connected to a light source.

4. The tissue visualization and modification device of claim 1, wherein the first illumination element is a light source located at the distal end of the elongated member.

5. The tissue visualization and modification device of claim 1, wherein the elongated member imaging sensor is a CMOS sensor.

6. The tissue visualization and modification device of claim 1, wherein the access body comprises stainless steel.

7. The tissue visualization and modification device of claim 1, wherein the irrigation channel is configured to deliver a therapeutic agent.

8. The tissue visualization and modification device of claim 1, wherein the first illumination element further comprises a diffusion element configured to provide uniform illumination of the tissue.

9. The tissue visualization and modification device of claim 1, further comprising a calibration element configured to remove image distortion from an image collected by the access body imaging sensor or the elongated member imaging sensor.

10. The tissue visualization and modification device of claim 1, wherein the elongated member imaging sensor is oriented to provide a field of view at an angle from the longitudinal axis.

* * * * *

UNITED STATES PATENT AND TRADEMARK OFFICE
CERTIFICATE OF CORRECTION

PATENT NO. : 10,045,686 B2
APPLICATION NO. : 13/739664
DATED : August 14, 2018
INVENTOR(S) : Xiaolong OuYang et al.

Page 1 of 1

It is certified that error appears in the above-identified patent and that said Letters Patent is hereby corrected as shown below:

In the Drawings

Sheet 6 of 6, (Reference Numeral 64a), (Fig. 6), Line 1, change "Undistortd" to --Undistorted--.

Sheet 6 of 6, (Reference Numeral 64b), (Fig. 6), Line 1, change "Undistortd" to --Undistorted--.

In the Specification

Column 6, Line 64, change "OminVision" to --OmniVision--.

Signed and Sealed this
Twentieth Day of November, 2018

Andrei Iancu
*Director of the United States Patent and Trademark Office*